United States Patent [19]

Quante et al.

[11] Patent Number: 5,516,902
[45] Date of Patent: May 14, 1996

[54] PROCESS FOR PREPARING CEPHALOSPORIN COMPOUNDS

[75] Inventors: J. Michael Quante, Durham; Randal A. Hoke, Cary; Patrick D. Mize, Durham; Daniel L. Woodard, Raleigh; O. Elmo Millner, deceased, late of Durham, all of N.C., by Margaret Millner, legal representative

[73] Assignee: Becton, Dickinson and Company, Franklin Lakes, N.J.

[21] Appl. No.: 227,168

[22] Filed: Apr. 14, 1994

Related U.S. Application Data

[62] Division of Ser. No. 828,093, Jan. 30, 1992, Pat. No. 5,338,843.

[51] Int. Cl.⁶ .................................................. C07D 501/04
[52] U.S. Cl. ........................................................ 540/222
[58] Field of Search ............................ 540/222; 514/202, 514/210

[56] References Cited

U.S. PATENT DOCUMENTS 5,043,334  8/1991  Bell et al. ............................ 540/222

*Primary Examiner*—Nicholas Rizzo
*Attorney, Agent, or Firm*—Donna R. Fugit

[57] ABSTRACT

Chromogenic and fluorogenic substrates for β-lactamase, methods for synthesis thereof and methods for detecting β-lactamase in a sample are provided. The substrates are substantially colorless or substantially nonfluorescent β-lactam compounds which include an electronegative leaving group. The leaving group comprises a carbamate, carbonate, thiocarbamate or thiocarbonate linkage and a fluorescent moiety or a moiety capable of producing a visually detectable colored product. Upon cleavage of the lactam ring by β-lactamase, the leaving group is liberated and fluorescence or a colored product is produced.

3 Claims, 3 Drawing Sheets

PROCESS FOR PREPARING CEPHALOSPORIN COMPOUNDS

This is a division of application Ser. No. 07/828,093, filed Jan. 30, 1992, now U.S. Pat. No. 5,338,843.

FIELD OF THE INVENTION

This invention relates to the synthesis of chromogenic and fluorogenic substrates for β-lactamase and their use in assaying for the presence of β-lactamase in a sample.

BACKGROUND OF THE INVENTION

The β-lactamases are a group of enzymes which are produced by certain bacteria and confer resistance to β-lactam antibiotics. Such resistance has implications in the therapy of bacterial infections with β-lactam antibiotics, since bacterial resistance to the antibiotic may be of sufficient magnitude to cause the therapy to fail. It is therefore desirable to have available accurate and sensitive assays for the presence of β-lactamases in order to select an appropriate antibiotic therapy for a patient and to monitor patients receiving β-lactam therapy for the emergence of bacterial resistance due to production of β-lactamases.

β-lactamases confer resistance by hydrolysis of the β-lactam ring of the antibiotic. Ring hydrolysis results in inactivation of the β-lactam antibiotic. Enzymatic hydrolysis is believed to be initiated by the attack of a serine hydroxyl in the active site of the enzyme which opens the β-lactam ring and produces an acyl-enzyme intermediate. The acyl intermediate may be broken down by either one of two pathways depending on the stability and steric bulk of the leaving group. The two pathways of breakdown of the acyl intermediate are illustrated in FIG. 1. If the leaving group, X-Y, cannot be eliminated or is eliminated only very slowly the breakdown of the acyl-enzyme intermediate proceeds by pathway A in which the leaving group, X-Y, is eliminated after the enzyme is deacylated. This results in a high turnover of enzyme substrate (i.e., the antibiotic) and is therefore desirable for development of a sensitive detection system for β-lactamases.

When the leaving group is eliminated rapidly, the breakdown of the acyl-enzyme intermediate occurs by pathway B in which the elimination occurs before the enzyme is deacylated. This produces a more stable acyl-enzyme intermediate which hydrolyzes slowly to regenerate free enzyme. Incubation of β-lactamase with substrates of this type results in an initial burst of enzyme activity, followed by β-lactamase being nearly completely inactivated.

Elimination of the leaving group may not occur exclusively by only one of these alternative pathways. β-lactamase substrates which have a 3' leaving group generally are believed to be hydrolyzed to varying extents by both pathways.

Research in the field of synthesizing substrates for β-lactamase has primarily concentrated on developing compounds which are hydrolyzed by pathway B (FIG. 1) which results in enzyme inactivation. Most of the known chromogenic substrates for β-lactamase have been synthesized by modification of cephalosporins and have a 3' leaving group which is eliminated during hydrolysis of the lactam ring. These compounds tend to inhibit enzyme activity or deactivate the enzyme and therefore allow β-lactam antibiotics to inhibit the growth of the bacteria. However, such substrates have the disadvantage of reduced sensitivity when used in assays for β-lactamase as compared to substrates such as those herein disclosed.

While not wishing to be bound by any particular reaction mechanism, Applicants believe that the β-lactamase substrates of the present invention are hydrolyzed primarily by the first pathway, since the leaving groups are relatively bulky and would be eliminated slowly. Once cleaved, the leaving groups are fluorescent, visible or capable of producing a visually detectable color in an assay. These compounds therefore provide improved assay sensitivity over conventional reagents and, in addition, can be detected using fluorometric and spectrophotometric detectors commonly available in clinical laboratories. In particular, the inventive fluorogenic substrates represent an improvement over prior art β-lactamase substrates in that they fluoresce at a wavelength range which can be detected using such automated fluorescence detecting systems, making assays using such substrates more practical and economical when a large number of tests are to be performed, for example in a clinical laboratory. The inventive substrates which are capable of producing visually detectable colors upon cleavage provide an advantage over previously known β-lactamase substrates in that the leaving group can be further reacted to produce an insoluble dye which can be precipitated on a solid surface (e.g., a membrane) where it can be easily visualized.

Substrates for β-lactamase which are nonfluorescent prior to cleavage of the β-lactam ring and fluorescent after cleavage are described in U.S. Pat. No. 4,965,193 to Chen and U.S. Pat. No. 4,740,459 to Chen et al. The disclosed substrates are β-lactam antibiotics having an acyl side chain containing an α-amino group and an α-phenyl group or its derivatives. In the presence of β-lactamase, the amide bond is cleaved and the resulting open-ring compound fluoresces. In U.S. Pat. No. 4,965,193 it is further disclosed that fluorescence can be improved using a fluorescence developer which consists of a mild oxidizing agent and formaldehyde. These compounds differ from those of the present invention by virtue of the fact that the antibiotic itself becomes fluorescent when the β-lactam ring is opened, whereas the fluorogenic compounds of the invention release a leaving group which fluoresces. The substrates of the invention are therefore useful in fluorescence assays regardless of the structure of the acyl side chain. In addition, the inventive fluorogenic substrates require no post cleavage chemical treatment and are therfore amenable to providing kinetic information.

Chromogenic precipitating substrates for β-lactamase are disclosed in U.S. Pat. No. 4,978,613 to Bieniarz et al. These substrates include a moiety, $R_2$, linked to a β-lactam compound by a thioester linkage. This moiety, together with the sulfur atom to which it is attached, forms a sulfur-containing leaving group, S-$R_2$, the conjugate acid of which has a p$K_a$ less than 8. The leaving group is eliminated upon cleavage of the β-lactam ring by β-lactamase and reacts with a tetrazolium salt to form a colored precipitate without further breakdown of S-$R_2$. The chromogenic substrates of Bieniarz et al. are therefore limited to chromogens which have a sulfur atom for formation of the thioether or thioester linkage to the β-lactam compound. In contrast, the β-lactamase substrates of the present invention contain carbamate, carbonate, thiocarbamate or thiocarbonate linkages and can therefore be synthesized using non-sulfur-containing chromogens.

U.S. Pat. Nos. 3,355,452 and 3,484,437 to Urech et al. disclose derivatives of 7-amino-cephalosporanic acid which are synthesized by reaction of desacetyl-7-amino-cephalosporanic acid with an isocyanic ester. These semi-synthetic antibiotics, however, do not include a chromogenic or fluorescent leaving group and are resistant to cleavage by penicillinases and cephalosporinases. They are therefore not suitable as substrates for use in assays for β-lactamase such as those assays presently described.

SUMMARY OF THE INVENTION

The present invention provides rapid colorimetric and fluorogenic methods for detection of β-lactamase and chromogenic and fluorogenic substrates for use in such methods. The inventive chromogenic substrates may either produce a visually detectable color directly upon hydrolysis by β-lactamase or hydrolysis may be coupled to a second reaction in which a colored product is formed. The substrates of the invention have the following general structure:

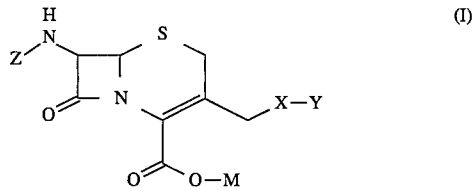

wherein the compound (I) is substantially colorless or substantially nonfluorescent. X is a functional group of atoms which, either alone or in concert with Y, is electronegative such that X-Y behaves as a leaving group. Y is a moiety which, upon release from the X-Y leaving group, is fluorescent, visible or capable of producing a visually detectable colored product. Preferably, the X moiety forms a carbamate, carbonate, thiocarbamate or thiocarbonate linkage between the cepham ring system and the leaving group which is liberated upon hydrolysis of the lactam ring by β-lactamase. Z is any of the moieties associated with this position in the known cepham type of β-lactam antibiotics. M may be hydrogen, a metal cation or an organic cation.

The liberated X-Y moiety undergoes further breakdown to X and Y. Depending on the structure of the leaving group, X may be, for example, $CO_2$, CSO or $CS_2$. Y, directly or by reaction with additional reagents, generates a visually detectable colored product or fluorescence. The generalized reaction scheme for cleavage of the β-lactam ring and elimination of X-Y is illustrated in FIG. 2.

Where Y reacts with additional reagents to produce a color, the additional reagents may include, for example, diazonium salts, oxidizing agents (such as atmospheric oxygen) and charge transfer or free radical initiators.

The inventive β-lactamase substrates are synthesized by reacting the desacetyl cepham antibiotic with the isocyanate or isothiocyanate of Y in the presence of organic solvents such as dimethyl formamide and recovering the product by precipitation, crystallization or chromatography.

DETAILED DESCRIPTION OF THE INVENTION

The chromogenic and fluorogenic β-lactamase substrates of the present invention are derivatives of the cepham type of β-lactam antibiotics and have the following general structure:

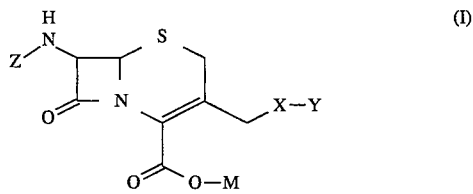

wherein the compound (I) is substantially colorless or substantially nonfluorescent; Z is any of the groups found in that position in the known cepham type of β-lactam antibiotics; M is a metal, an organic cation or hydrogen; and X-Y is a moiety which forms a leaving group which is eliminated when the β-lactam ring is cleaved by β-lactamase.

Z may be any one of the side groups found in that position in the cepham type of β-lactam antibiotics and will vary depending on the antibiotic selected to be derivatized. Examples are the cephalosporins and their derivatives. Cepham structures, including the characteristic Z side groups, may be found in *AHFS Drug Information* 91, Gerald K. McEvoy, Ed., published by the American Society of Hospital Pharmacists. Preferably, Z is

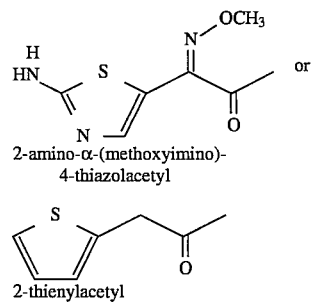

2-amino-α-(methoxyimino)-
4-thiazolacetyl or 2-thienylacetyl

M Will also vary depending on the salt of the β-lactam antibiotic selected for derivitization and may be a metal, an organic cation or hydrogen. Preferably, M is hydrogen, or sodium or potassium ion.

Y is a moiety which when linked to the β-lactamase substrate is substantially nonfluorescent, colorless or nonchromogenic. Elimination of the group X-Y from the substrate as a result of cleavage of the β-lactam ring by β-lactamase and further spontaneous breakdown of X-Y into X+Y allows Y to fluoresce or to produce a visible colored product. Examples of Y include

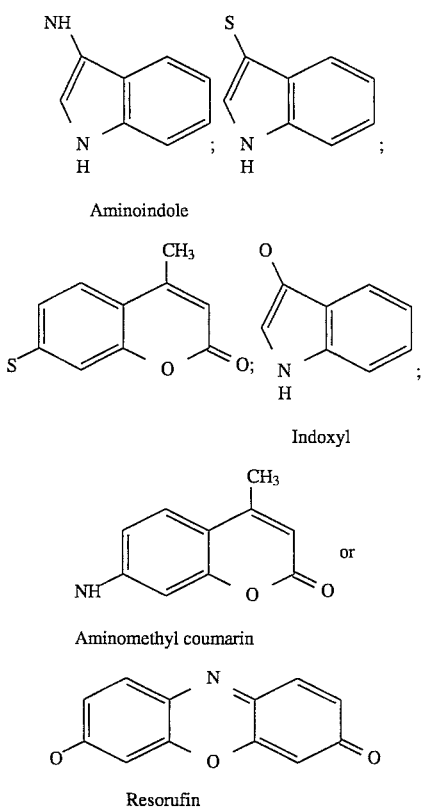

Additional examples of Y suitable for use in the compounds of the invention are well known in the art of chromogenic and fluorogenic substances. These include, but are not limited to, 1-naphthol, 2-naphthol, naphthylamines, fluoresceins, N-methyl indoxyl, 4-methyl umbelliferone, 1-methyl-7-hydroxyquinolinium iodide, rhodamine, p-nitrophenol and o-nitrophenol Preferably, Y is aminomethyl coumarin (AMC), aminoindole or indoxyl.

X is a group of atoms which, alone or in conjunction with Y, is electronegative such that X-Y acts as a leaving group which is eliminated when the β-lactam ring is cleaved by β-lactamase. Preferably, X is a functional group having the following general structure:

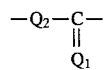

wherein $Q_1$ and $Q_2$ are preferably oxygen and/or sulfur.
Preferred X moieties are:

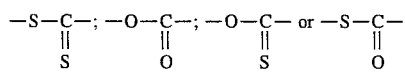

Figure 1:
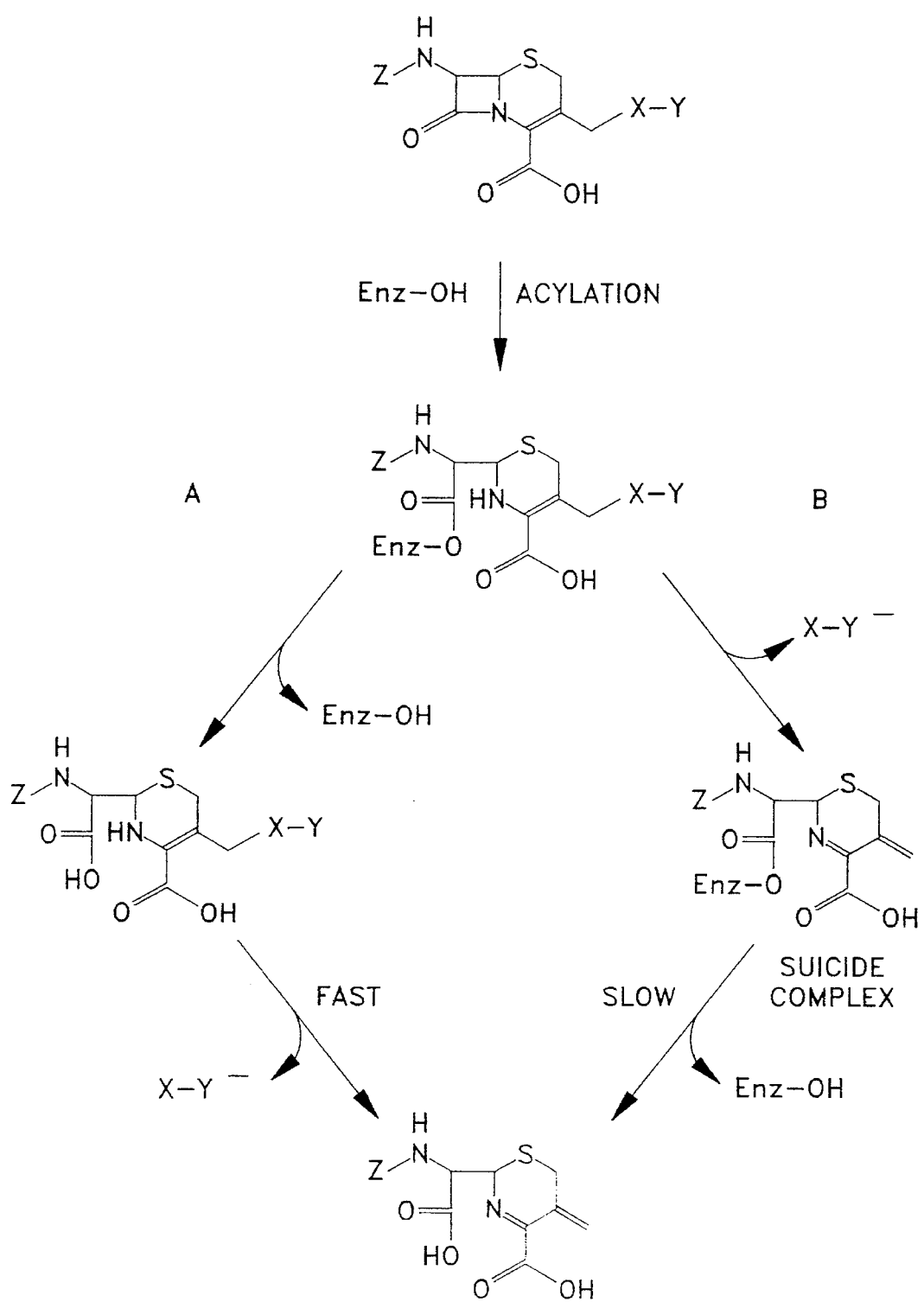
FIG. 1 is an illustration of the mechanism of hydrolysis of the β-lactam ring by β-lactamase, showing the two pathways by which the acyl-enzyme intermediate may be broken down.
Figure 2:
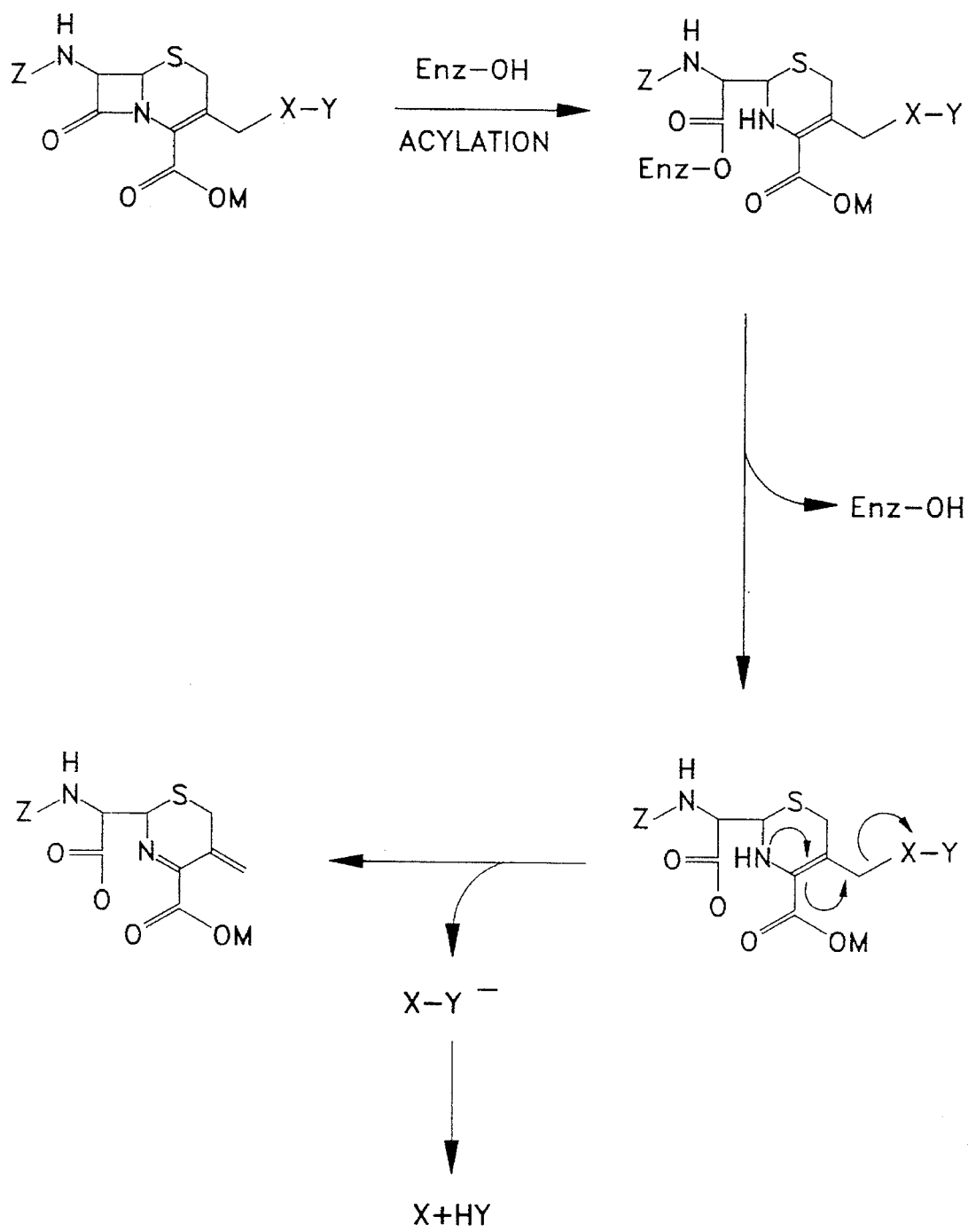
FIG. 2 is an illustration of the mechanism of cleavage of the inventive β-lactamase substrates by β-lactamase, showing elimination of the X-Y leaving group and subsequent further breakdown of X-Y to X and Y.
Figure 3:
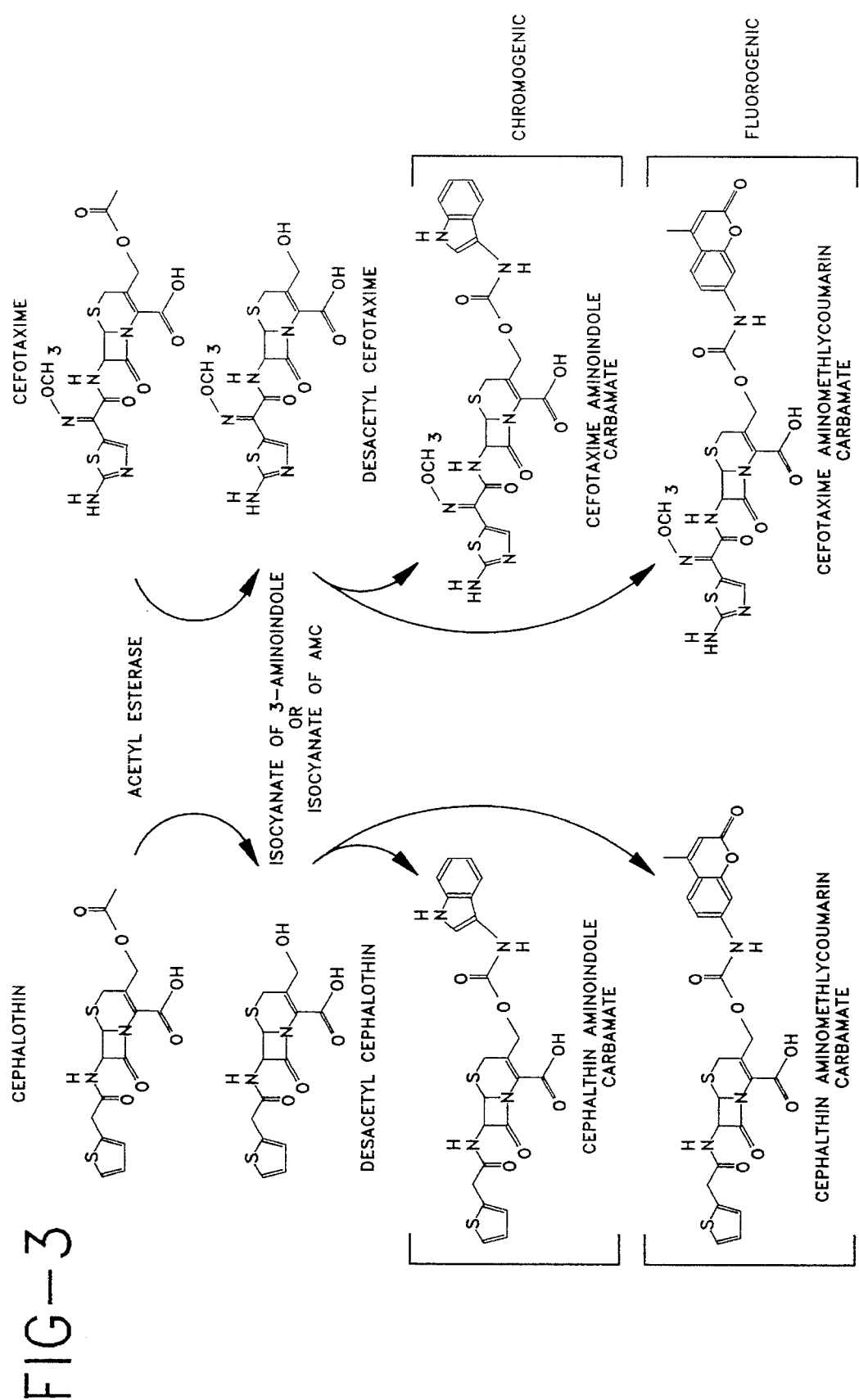
FIG. 3 is an illustration of the methods of synthesis of cephalothin aminoindole carbamate, cefotaxime aminoindole carbamate, cephalothin aminomethylcoumarin carbamate and cefotaxime aminomethylcoumarin carbamate.

For the preparation of the inventive β-lactamase substrates wherein Y contains a reactive nitrogen, the desacetyl cepham antibiotic is reacted with the isocyanate or isothiocyanate of Y in the presence of organic solvents such as dimethyl formamide and recovering the product by precipitation or by crystallization. Preferred β-lactamase substrates are synthesized by reaction of desacetyl cephalothin or desacetyl cefotaxime with 3-aminoindole isocyanate or 7-isocyano-4-methyl coumarin to produce the respective aminoindole carbamates and AMC carbamates. These reaction schemes are illustrated in FIG. 3. Cephalothin indoxyl carbonate substrates are synthesized by reaction of desacetyl cephalothin with indoxyl-3-chlorocarbonate.

Several methods of preparation of C-10 deacetyl cephams for use in the syntheses of the present invention are known in the art. (JACS 107, 4766 (1985); Biochem J. 81, 591 (1961)) Preferably, the C-10 desacetyl cephams are synthesized by a modification of the methods disclosed by Mobashery and Johnston (Tet. Lett. 27 (29), 3333–3336 (1986)). Briefly, this method involves placing the acetyl cepham in the presence of acetyl esterase and controlling the pH, especially between pH 4.5 and 7.5, and then after a period of time when the pH has stabilized storing the enzyme acetyl cepham mixture at 4° C. overnight.

When X-Y is a leaving group containing a Y moiety such as aminoindole or indoxyl, a colorimetric assay for β-lactamase can be performed by coupling the generation of aminoindole or indoxyl from the breakdown of X-Y to reactions with additional reagents to produce a visually detectable colored product. The additional reagents may be, for example, diazonium salts, oxidizing agents, or charge transfer and free radical initiators, such as fast red TR salt, fast BB salt, fast red violet salt, molecular oxygen, nitro blue tetrazolium, or other fast red or fast blue salts or other tetrazolium compounds. The color of the product will depend on the reagent selected and its concentration. Preferably, hydrolysis of the β-lactam ring of the chromogenic substrate releases 3-aminoindole, a precipitating dye marker, and the reaction is coupled to a diazonium reagent or nitroblue tetrazolium (NBT). The color of the precipitate depends on the diazonium salt used.

The substrates of the invention react with β-lactamase in the presence of the diazonium coupling reagents without signficant inactivation of the enzyme if the concentration of the diazonium salt is equal to or less than about 1 mM. Preferably, to perform the assay the β-lactamase substrate is dissolved in DMSO or methanol and diluted in phosphate buffer pH 7.2 to a concentration of about 1–5 mM. The coupling reagents are similarly dissolved. Modifications and variations of such β-lactamase assays are within the ordinary skill in the art and are also suitable for use with the β-lactamase substrates disclosed herein. While such chromogenic assays may be performed in solution, it is preferred that the assay be performed on a membrane or filter such as nitrocellulose containing the chromogenic substrate. The filter is treated with the diazonium salt following cleavage of the substrate with β-lactamase. The membrane facilitates deposit of the colored precipitate for visualization. Such membrane assays also have the advantage of being adaptable for use in lifting bacterial colonies for screening for the presence of β-lactamase.

By way of example, the colored products produced by cefotaxime aminoindole carbamate substrates reacted with β-lactamase in the presence of saturated diazonium salt solutions or NBT in water are generally as follows:

| Coupling Reagents | Product Color |
| --- | --- |
| Fast Red TR salt | Red solution |
| Fast Blue BB salt | Blue soln./ppt. |
| Fast Red Violet LB salt | Orange soln./ppt. |
| 2-Methoxy-4-morpholino benzene diazonium Cl | Green soln./ppt. |
| Nitroblue tetrazolium | Dark ppt. |

Similarly, when X-Y contains indoxyl, released indoxyl dimerizes and is oxidized by molecular oxygen, thereby producing insoluble indigo dye which is visible in the assay or which can be detected using a spectrophotometer.

When Y is a fluorescent group, elimination of X-Y from the substrate and its further breakdown into X+Y allows Y to fluoresce in the presence of light of the appropriate wavelength. Y may be selected to fluoresce at any wavelength which is appropriate for a particular assay, but a Y moiety which excites/fluoresces at 365/440 nm (e.g., umbelliferone or aminomethyl coumarin containing) or 570/590 nm (e.g., resorufin containing) is preferred. The assay for β-lactamase may then be performed by exciting the fluorescent moiety and detecting the fluorescence emitted, either manually or using an automated system. Preferably, automated detection is used to facilitate reading of assay results and handling of multiple assays.

The compositions and methods set forth herein represent certain embodiments of the principles of the invention. It is to be understood that the present invention may be embodied in numerous alternative fashions and that such alternative embodiments may be conceived by those skilled in the art using only routine abilities and without departing from the spirit and scope of the invention. Specific illustrative embodiments are set forth in the following Examples but are not to be considered as limiting the scope of the invention as defined by the appended claims.

In the following examples, acetyl esterase (acetic acid hydrolase) partially purified from orange peels, was supplied by Sigma Chemical Co. (St. Louis, Mo.) in 2.5M ammonium sulfate containing 0.1M sodium oxalate. The solution contained 10.3 units of acetyl esterase per mg and 25 units pectinesterase per mg of protein. Cephalothin sodium salt was supplied by Sigma Chemical Co. Cefotaxime sodium salt was supplied by CALBIOCHEM (La Jolla, Calif.). 20% phosgene in toluene was supplied by Fluka Chemical Corp (St. Louis, Mo.). Benzene was supplied by Fisher Scientific (Pittsburgh, Pa.). Reverse phase silica gel was supplied by J. T. Baker Inc. (Phillipsburg, N.J.). Nitrocefin was supplied by Becton Dickinson Microbiology Systems (Cockeysville Md.). All other chemicals and reagents were supplied by Aldrich Chemical Co. (Milwaukee, Wis.). Commercial materials and reagents were used without further purification.

IR spectrometry was performed with a Perkin-Elmer 283B Spectrometer, Perkin-Elmer Corp. (Norwalk, Conn.). Melting points were obtained with a Thomas-Hoover capillary melt point apparatus (Philadelphia, Pa.) and are uncorrected. NMR spectra were obtained on an IBM-Bruker WP-200SY (200 mHz) (Billerica, Mass.). Chemical shifts are reported in ppm relative to tetramethylsilane. Elemental analysis were performed by Galbraith Laboratories Inc. (Knoxville, Tenn.). HPLC analysis was determined using a Waters HPLC system employing dual 510 pumps, WISP 710B or U6K injectors, Waters 990-MS photodiode array detector or model 441 absorbance detector, and a Waters 860 data system. A Brownlee Spheir-5 RP-18 220×4.6 MM column was used. The solvent system was 60% solvent A and 40% solvent B, using isocratic flow at 0.5 mL/min. Solvent A contained 95% water, 5% acetonitrile, and 0.2% trifluoroacetic acid. Solvent B contained 95% acetonitrile, 5% water, and 0.2% trifluoroacetic acid.

EXAMPLE 1

SYNTHESIS OF REAGENTS

A. DESACETYL CEPHALOTHIN

A 125 mL erlenmeyer flask, fitted with magnetic stirrer, was charged with 2.0 g (4.78 mMol) of Cephalothin sodium salt and 75 mL of water was incubated at 37 C. in an isothermal water bath. The pH was adjusted to 6.6 using 0.2N NaOH. With constant stirring acetyl esterase (1000 units) was dissolved in 10 mL water, and added to the cephalothin sodium salt solution in one portion. The pH immediately decreased and was maintained between 6.7 and 6.4 using 0.2N NaOH over the entire course of the reaction. After approximately 3 hours the pH of the solution changed at a much slower rate. HPLC analysis indicated only a small amount of cephalothin remaining. The reaction mixture was stored at 4° C. for 3 days at which time HPLC showed absence of starting material. After lyophilization, the pure product was isolated by reverse phase column chromatography (methanol/water).

Product Analysis: NMR ($d_6$DMSO) Carbonyl Carbons: 169.8, 165.1, 163.0 ppm. Vinyl and Aromatic Carbons: 137.2, 132.1, 126.5, 126.1, 124.6, 121.9 ppm. All Other Carbons: 61.8, 58.3, 56.8, 38.7, 26.4 ppm. HPLC retention time; desacetyl cephalothin - 7.10 min, cephalothin - 8.6 min. Reverse Phase TLC 6:4 methanol:water $R_f$; desacetyl cephalothin - 0.914.

B. DESACETYL CEFOTAXIME

Desacetyl cefotaxime was prepared in a similar manner as described above except that the reaction was complete after 1.5 hr. Following lyophilization, the pure product was obtained by reverse phase column chromatography (methanol/water).

Product Analysis: NMR ($d_6$DMSO) Carbonyl Carbons: 170.0, 166.6, 163.3, 162.9 ppm. Aromatic and vinyl carbons 149.8, 143.0, 131.8, 121.4, 109.9 ppm. All other carbons 73.3, 62.8, 61.4, 61.0, 59.1 ppm. HPLC retention time; desacetyl cefotaxime - 6.30 min, cefotaxime - 7.30 min. Reverse phase TLC solvent 6:4 methanol:water $R_f$=0.933.

C. INDOLE-3-HYDRAZIDE

A three neck round bottom flask fitted with a condenser with argon outlet, addition funnel, and argon inlet, was oven dried at 132° C. for 2 h, then heat dried while purging with argon. The apparatus was allowed to cool to room temperature under argon then charged with 500 mL benzene via oven dried syringe, followed by 3.0 g indole-3-carboxylic acid (18.6 mMol). The solid was insoluble at room temperature. 5.5 mL thionyl chloride was added (74.4 mMol, 4.0 eq) slowly via the addition funnel. The resulting solution was refluxed overnight, at which time all the solid had dissolved. The reaction mixture was cooled to ambient temperature and 4.6mL anhydrous hydrazine (148.8 mMol, 8 eq.) was added. A precipitate immediately formed, which was filtered and dried under reduced pressure overnight. The pure hydrazide was obtained by normal phase column chromatography, using a mixture of 9:1 methylene chloride:methanol (77% yield).

Product Analysis: NMR ($d_6$DMSO) - carbonyl carbon 165.1 ppm. aromatic and vinyl carbons 135.9, 127.0, 126.1, 121.7, 120.8, 120.2, 111.7, 108.9 ppm. Elemental analysis ($C_9H_9N_3O$); Calculated: C 61.71, H 5.14, N 24.00. Found: C 61.51; H 5.03; N 24.23. Normal phase TLC 95:5 Methylene chloride:methanol $R_f$=0.45.

D. INDOLE-3-AZIDE

A round bottom flask fitted with magnetic stirrer was charged with 400 mg indole-3-hydrazide (2.3 mMol) and 50 mL of 50% glacial acetic acid aqueous solution. After stirring 15 minutes the solution was filtered. The supernate was cooled to 0° C. in a ice bath and 0.5 g sodium nitrate, dissolved in 1 mL of water, was added. A precipitate formed immediately. The reaction was stirred for 2 hr allowing the temperature to return to ambient temperature. The reaction mixture was filtered and the precipitate was washed with cold water (3×5 mL) and methanol (3×5 mL). The product was stored under reduced pressure overnight.

Product Analysis: Crude yield 82%. NMR (d$_6$DMSO) carbonyl carbon 167.1 ppm. Aromatic and vinyl carbons 138.2, 135.0, 125.3, 124.6, 123.4, 121.2, 113.8, 108.9 ppm. IR N$_3$ 2160; CO 1680; NH Indole ring 3250 cm$^{-1}$. Elemental analysis (C$_9$H$_5$N$_{4O}$) Calculated: C 58.06; H 3.22; N 30.10. Found: C 58.19; H 3.04; N 30.17. Reverse phase TLC 95:5 methylene chloride:methanol R$_f$=0.714.

E. INDOLE-3-ISOCYANATE

A three neck round bottom flask fitted with addition funnel, condenser with argon outlet, and argon inlet, was oven dried for 2 hr, then heat dried while purging with argon, and cooled to ambient temperature while continuing to purge with argon. The apparatus was charged with 350 mg of indole-3-azide (1.9 mMol) and 40 mL anhydrous toluene and refluxed until TLC analysis shows that the indole-3-azide was completely consumed (approximately 3 hr). The toluene was removed under reduced pressure resulting in a solid. This solid was stored under reduced pressure overnight to remove traces of toluene. The product was compared to known samples, and no further attempts were made to purify the product.

Product Analysis: IR NCO 2300 cm$^-$; NH Indole 3400 cm$^{-1}$. Reverse phase TLC 95:5 methylene chloride:methanol R$_f$=0.786. Melting Point 52°–54° C.

F. 7-ISOCYANO-4-METHYL COUMARIN

A three neck round bottom flask fitted with an argon inlet, an addition funnel with rubber septum, and a dry ice condenser attached to a sodium hydroxide scrubber, was heat dried while purging with argon for 10 min, and cooled to ambient temperature under argon. The apparatus was charged with 2.0 g of 7-amino-4-methyl coumarin (11.4 mMol), 100 mL p-dioxane via an oven dried syringe followed by 15 mL 20% phosgene in toluene (28.95 mMol). The mixture was refluxed strongly for 2 hr, 15 mL of 20% phosgene in toluene was added; refluxed an additional 6 hr, and cooled to ambient temperature. The dry ice was allowed to evaporate overnight under a stream of argon which purged the excess phosgene from the system. The toluene and p-dioxane were removed under reduced pressure at 40° C. resulting in a yellow solid. The pure product was obtained by the addition of 100 mL of chloroform and stirring for 15 min. to dissolve the isocyanate. Followed by filtration (to remove AMC HCl), and removal of solvent under reduced pressure. The solid was stored under reduced pressure overnight.

Product Analysis: IR NCO peak at 2280 cm.

EXAMPLE 2

SYNTHESIS OF CEPHALOTHIN AMINOINDOLE CARBAMATE

A three necked round bottom flask fitted with argon inlet, argon outlet, and a rubber septum was oven dried overnight then purged with argon for thirty min. The apparatus was charged with 1 g desacetyl cephalpthin (2.66 mMol - prepared according to Example 1A) dissolved in 20 ml DMF followed by 0.46 g Indole-3-isocyanate (3.19 mMol 1.2 eq - prepared according to Example 1E) dissolved in the minimum amount of DMF. The resulting mixture was stirred at 28° C. overnight. The pure product was obtained by crystallization from the reaction mixture by the addition of ethyl acetate.

Product Analysis: NMR (d$_6$DMSO) Carbonyl carbons 170.4, 170.0, 164.2, 163.0 ppm. Aromatic and vinyl carbons 138.6, 136.6, 135.1, 128.6, 127.0, 126.8, 125.4, 125.2, 122.0, 120.1, 118.6, 113.4, 111.8, 101.5 ppm. All other carbons 65.2, 58.5, 57.8, 45.8, 26.6 ppm. Elemental analysis C$_{23}$H$_{20}$N$_4$O$_6$S$_2$ C 53.91; H 3.91; N 10.94. Found C 53.85; H 4.07; N 10.79. Reverse phase TLC solvent 6:4 methanol:water R$_f$=0.575.

EXAMPLE 3

SYNTHESIS OF CEFOTAXIME AMC CARBAMATE

A three neck round bottom flask fitted with argon inlet, argon outlet, and rubber septum was oven dried for 2 h then purged with argon for 30 min. The apparatus was charged with 500 mg desacetyl cefotaxime (1.15 mMol - prepared as in Example 1B) dissolved in 17 mL anhydrous dimethyl formamide followed by 462 mg 4-methyl-7-isocyano coumarin (2.30 mMol - prepared as in Example 1F) dissolved in 10 mL dimethyl formamide. The reaction was stirred at 30° C. for 48 h at which time TLC shows all starting desacetyl cefotaxime had completely reacted. The product was precipitated from the reaction mixture by the addition of about 50 mL of 20% acetone/80% ethyl acetate. The solid was isolated by filtration under argon and washed with 3×5 mL 20% acetone/80% ethyl acetate. The solid was stored under reduced pressure overnight.

Product Analysis: Elemental analysis C$_{25}$H$_{22}$N$_6$O$_9$S$_2$: C 48.86; H 3.58; N 13.68. Found C 50.01; H 3.48; N 13.62. Reverse phase TLC 6:4 methanol/water R$_f$=0.694. NMR(d$_6$DMSO) 6 carbonyl carbons 172.0, 171.0, 166.0, 164.2, 154.3; 13 aromatic or vinyl carbons 154.6, 154.0, 138.7, 135.3, 126.6, 126.2, 126.1, 124.9, 114.0, 112.1, 109.3, 107.3, 98.1; 6 other carbons 64.6, 58.7, 56.6, 36.7, 21.3, 17.3 ppm.

EXAMPLE 4

SYNTHESIS OF CEPHALOTHIN AMC CARBAMATE

A three neck round bottom flask fitted with argon inlet, argon outlet, and rubber septum was oven dried for 2 h then purged with argon for 30 min. This apparatus was charged with 500 mg desacetyl cephalothin (1.33 mMol - prepared according to Example 1A) dissolved in 17 mL anhydrous dimethyl formamide followed by 400 mg 4-methyl-7-isocyano coumarin (1.99 mMol - prepared according to Example 1F) dissolved in 10 mL dimethyl formamide. The reaction was stirred at 30° C. for 48 h at which time TLC shows all starting desacetyl cephalothin had completely reacted. The product was precipitated from the reaction mixture by the addition of about 50 mL of 20% acetone/80% ethyl acetate. The solid was isolated by filtration under argon and washed with 3×5 mL 20% acetone/80% ethyl acetate. The solid was stored under reduced pressure overnight.

Product Analysis: Elemental analysis C$_{25}$H$_{21}$N$_3$O$_8$S$_2$: C 54.05; H 3.78; N 7.57. Found C 54.09; H 3.07; N 7.64. Reverse phase TLC solvent 6:4 methanol:water R$_f$=0.657. NMR (d$_6$DMSO) 5 carbonyl carbons 168.7, 165.7, 163.0, 162.3, 161.0 ppm; 14 aromatic carbons 148.3, 143.0, 127.0, 118.7, 118.3, 117.7, 116.7, 114.7, 114.0, 111.3, 109.0, 108.5, 108.0, 98.3 ppm; 6 other carbons 62.7, 62.0, 61.7, 58.0, 17.7 ppm.

EXAMPLE 5

SYNTHESIS OF CEFOTAXIME INDOLE CARBAMATE

A three neck round bottom flask fitted with argon inlet, argon outlet, and rubber septum was oven dried for 2 h then purged with argon for 30min. This apparatus was charged with 500 mg desacetyl cefotaxime (1.15 mMol - prepared according to Example 1B) dissolved in 17 mL anhydrous dimethyl formamide followed by 0.22 g indole-3-isocyanate (1.3 eq. 1.49 mMol - prepared according to Example 1E) dissolved in 10 mL dimethyl formamide. The reaction was stirred at 30° C. for 48 h at which time TLC showed all starting desacetyl cefotaxime had completely reacted. The product was precipitated from the reaction mixture by the addition of about 50 mL of ethyl acetate. The solid was isolated by filtration under argon and washed with 3×5 mL cold ethyl acetate. The solid was stored under reduced pressure overnight.

Product Analysis: NMR ($d_6$DMSO) Carbonyl carbons 174.3, 169.8, 167.2, 164.2, 164.0 ppm. Aromatic and vinyl carbons 150.0, 143.3, 136.3, 131.6, 128.2, 125.0, 121.6, 120.8, 120.1, 119.0, 111.1, 110.0, 101.2 ppm. All other carbons 73.7, 64.0, 62.1, 61.9, 58.5 ppm. Elemental analysis $C_{23}H_{21}N_7O_7S_2$:C48.34; H 3.68; N 17.16. Found C 48.08; H 3.62; N 17.05. Reverse phase·TLC solvent 6:4 methanol:water $R_f$=0.840.

Cephalothin indole carbamate was synthesized using a similar procedure, substituting desacetyl cephalothin for desacetyl cefotaxime.

EXAMPLE 6

KINETIC RATE DETERMINATIONS

The fluorogenic β-lactamase substrates of the invention were tested for their ability to be hydrolyzed by β-lactamase with release of the fluorescent moiety. The kinetics of hydrolysis were compared to the kinetics of hydrolysis of nitrocefin. The two fluorogenic substrates tested were hydrolyzed using three mutant β-lactamases found in cephem resistant bacteria to compare the rate of hydrolysis with the wildtype enzyme, TEM-1 (Ambler. Phil. Trans. R. Soc. Lond. 289:321 (1980); Sougakoff et al. Reviews of Infectious Diseases 10:879 (1988)).

Nitrocefin kinetics were determined using a Hewlett-Packard 854A spectrophotometer with Chem Station programming, Hewlett-Packard Company Scientific Instruments Division (Palo Alto, Calif.). The data were fit to an unweighted Michaelis-Menten equation using the non-linear data regression package ENZFITTER (Elsevier-BIOSOFT, Cambridge, United Kingdom). The buffer used for all dilutions was 9:1 (50 mM phosphate buffer pH 7.2:DMSO), designated buffer A. The rate of hydrolysis for nitrocefin was determined at a range of 504–514 nm for 300 sec. Duplicates runs were performed and averaged for each concentration reported. A nitrocefin stock solution, containing 10.1 mg dissolved in 1 mL DMSO and diluted to 15 mL with buffer A was used for these runs. Rates were determined using from 1–0.004 mL of nitrocefin solution diluted to 1 mL total with buffer A. Rate determining experiments were done using 9 different concentrations of the nitrocefin solution and a 1:25 dilution of each enzyme in buffer A.

Fluorescence kinetics were determined on a Perkin-Elmer LS-5 fluorescence spectrometer Perkin-Elmer Corp. (Norwalk, Conn.) for a duration of 300 sec. Excitation and emission. wavelengths were set to 365 and 440 nm with. slits of 10 and 3 nm, respectively. Buffer A was used for all dilutions. Duplicates were done for each rate reported. Rates were determined using the following solutions: a) 10.8 mg cephalothin AMC carbamate dissolved in 1 mL of DMSO diluted to 15 mL with buffer A, and b) 11.9 mg cefotaxime AMC carbamate dissolved in 1 mL DMSO diluted to 15 mL with buffer A. For each experiment 0.1 mL of substrate solution was diluted to 3 mL with buffer A. To this was added 0.03 mL of enzyme solution containing (25:1 dilution of the enzyme in buffer A). Fluorescence was read for 300 sec. The rates were determined for both substrates at this concentration for all enzymes tested.

Both products were shown to produce a fluorometric response upon cleavage of the β-lactam ring with β-lactamase. The kinetic data obtained showed that the cephalothin AMC carbamate substrate was cleaved faster than the cefotaxime AMC carbamate by the wild type and all mutant enzymes. Cephalothin AMC carbamate was cleaved fastest by the 237 (SER) mutant enzyme followed closely by the wild type enzyme. The 104(LYS) mutant enzyme cleaved this substrate at a rate of about half that of the 237(SER) enzyme. The 238(SER) mutant enzyme cleaved the substrate most slowly.

The cefotaxime AMC carbamate substrate was cleaved most slowly by the wild type β-lactamase. In comparison, the 237(SER) mutant enzyme gave a 60% increase in hydrolysis rate. The 238(SER) and 104(LYS) mutations gave a greater than 100% increase in the rate of hydrolysis of this substrate.

The rates of hydrolysis for nitrocefin with each of the β-lactamase enzymes were also obtained. The 237(SER) mutant hydrolyzed nitrocefin the fastest, followed by wild type, then the 104(LYS) and 238(SER) mutants.

EXAMPLE 7

CLEAVAGE OF CHROMOGENIC SUBSTRATES

Cleavage of the β-lactam ring of cefotaxime indole carbamate or cephalothin indole carbamate produces a cascade of electron migration which releases 3-aminoindole. Addition of various diazonium salts to the reaction mixture following cleavage with β-lactamase produced a colored precipitate.

The β-lactamase substrates were absorbed onto a nitrocellulose membrane and used to detect the presence of the enzyme. A solution of the enzyme was added and after a brief incubation at room temperature, a solution containing the diazonium salt was added. A colored product was produced which was precipitated on the membrane.

This filter assay format can be adapted for use with the filter lift assay known in the art for screening bacterial colonies for the presence of β-lactamase. In such an assay, a membrane containing the chromogenic β-lactamase substrate of the invention can be used to lift bacterial colonies for screening. Following incubation on the membrane, addition of a solution of a diazonium salt with subsequent precipitation of a colored product on the membrane indicates the presence of β-lactamase in the bacterial colony.

What is claimed is:

1. A method of making cephalothin aminomethyl coumarin carbamate or cefotaxime aminomethyl coumarin carbamate comprising:

a) reacting desacetyl cefotaxime or desacetyl cephalothin with 4-methyl-7-isocyano coumarin in the presence of an organic solvent;

b) precipitating the cephalothin aminomethyl coumarin carbamate or the cefotaxime aminomethyl coumarin carbamate by addition of a mixture of acetone and ethyl acetate, and;

c) isolating the precipitated cephalothin aminomethyl coumarin carbamate or cefotaxime aminomethyl coumarin carbamate.

2. The method according to claim 1 wherein the β-lactamase substrate is precipitated by addition of 20% acetone/ 80% ethyl acetate.

3. The method according to claim 1 wherein the desacetyl cephalothin or desacetyl cefotaxime and 4-methyl-7-isocyano coumarin are reacted in the presence of dimethyl formamide.

* * * * *